United States Patent [19]

Nemet-Mavrodin et al.

[11] 4,402,794
[45] Sep. 6, 1983

[54] PURIFICATION OF BUTYLENE OXIDES BY EXTRACTIVE DISTILLATION WITH SELECTED EXTRACTIVE DISTILLATION SOLVENTS

[75] Inventors: Margaret I. Nemet-Mavrodin, Robbinsville; Yon-Li Shangkuan, Edison; Richard L. Bobeck, Princeton Junction, all of N.J.

[73] Assignee: Atlantic Richfield Company, Los Angeles, Calif.

[21] Appl. No.: 381,121

[22] Filed: May 24, 1982

[51] Int. Cl.³ .................... B01D 3/40; C07D 301/12; C07D 301/32
[52] U.S. Cl. ........................................ 203/14; 203/39; 203/70; 203/84; 549/529; 549/541
[58] Field of Search ............ 203/14, 70, 68, 69, 203/52, 84, 39; 549/529, 541

[56] References Cited

U.S. PATENT DOCUMENTS

| | | | |
|---|---|---|---|
| 2,779,721 | 1/1957 | Houtman et al. | 203/14 |
| 2,903,465 | 9/1959 | Suter et al. | 203/70 |
| 3,039,940 | 6/1962 | Prinz et al. | 203/70 |
| 3,338,800 | 8/1967 | Binning et al. | 203/70 |
| 3,464,897 | 9/1969 | Jubin | 549/541 |
| 3,523,956 | 8/1970 | Kaplan | 549/529 |
| 3,607,669 | 9/1971 | Jubin | 203/14 |
| 3,654,317 | 4/1972 | Harrod et al. | 549/529 |
| 3,843,488 | 10/1974 | Schmidt et al. | 203/70 |

Primary Examiner—Wilbur L. Bascomb, Jr.
Attorney, Agent, or Firm—Craig E. Larson

[57] ABSTRACT

A process for purifying 1,2-butylene oxide which comprises extractive distillation of crude butylene oxide with an added solvent comprising an acyclic, paraffinic hydrocarbon having from 7 to 9 carbon atoms.

12 Claims, 1 Drawing Figure

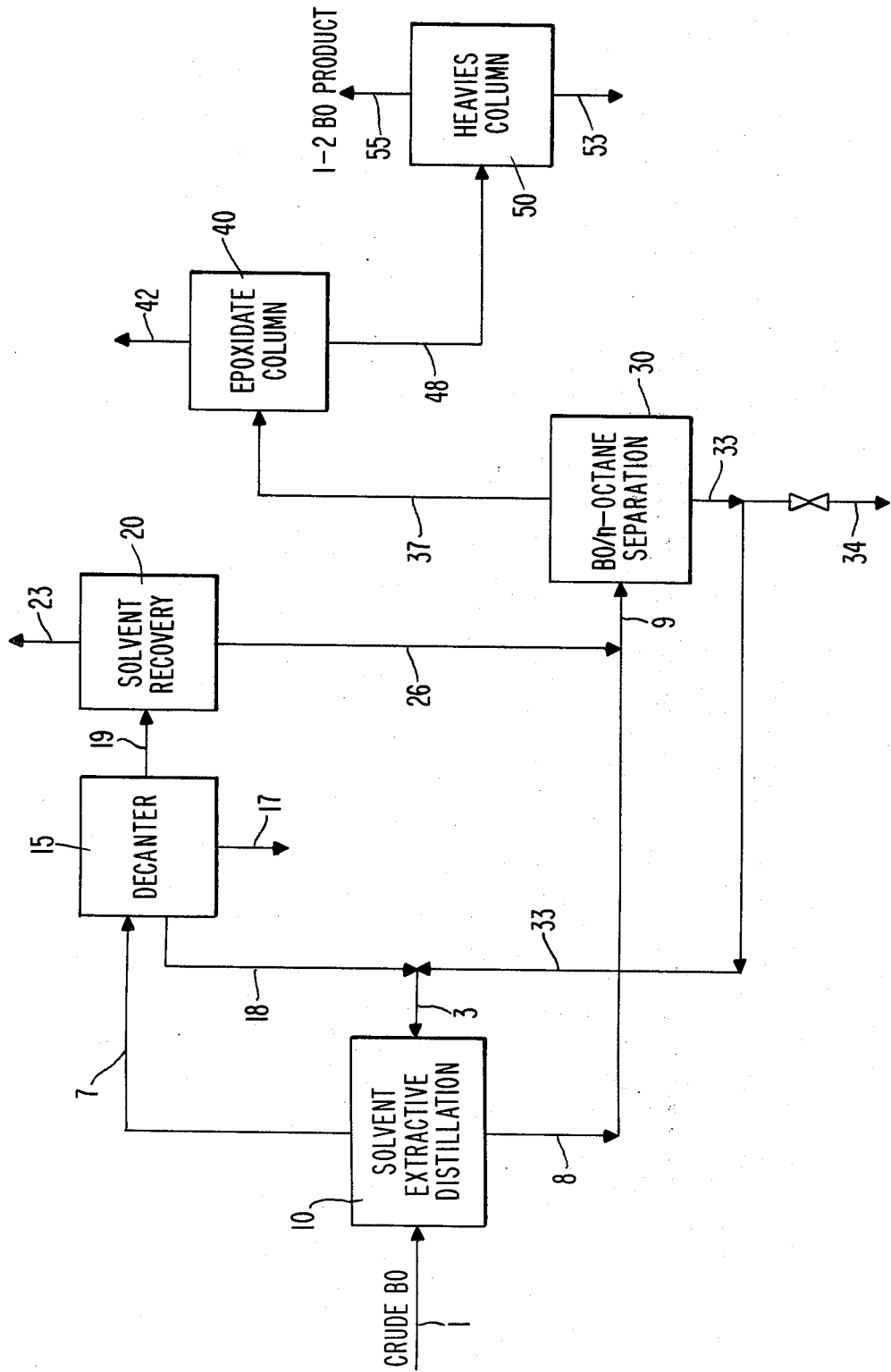

PURIFICATION OF BUTYLENE OXIDES BY EXTRACTIVE DISTILLATION WITH SELECTED EXTRACTIVE DISTILLATION SOLVENTS

BACKGROUND OF THE INVENTION

1. Field of the Invention

This invention relates to a method of removing water from butylene oxides. More particularly, this invention relates to drying 1,2-butylene oxide; cis- or trans-2,3-butylene oxide isobutylene oxide; or mixtures thereof. This invention also relates to a process for removing impurities from butylene oxides by subjecting a crude butylene oxide stream, which cannot be easily purified by conventional distillation processes, to extractive distillation with suitable solvents. This invention still further relates to the resolution of crude 1,2-butylene oxide-containing mixtures produced by the epoxidation of 1-butylene by an organic hydroperoxide.

2. Description of the Prior Art

Alkylene oxides may be prepared from olefins by direct oxidation with oxygen; by oxidation with an oxidizing agent such as hydrogen peroxide, peracetic acid, or an organic hydroperoxide; or by conversion of halohydrins (prepared from the olefins) by the action of the base. Alkylene oxides are useful as polymerizable monomers, but they must be in a highly pure form for this purpose.

Alkylenes oxides obtained by direct oxidation or by oxidation with an oxidizing agent contain impurities including water and oxygen-containing organic compounds such as aldehydes, ketones, esters, alcohols, inorganic esters. Suggested methods for removing impurities include distillation (as well as extractive distillation) and chemical treatments. An example of the latter method is hydrolysis of esters and neutralization of acids with an alkali solution followed by distillation. Chemical treatments are generally undesirable because of associated product losses.

Purification of butylene oxides by means of distillation alone is difficult because of close-boiling impurities and formation of azetropic mixtures. Unlike ethylene or propylene oxides, butylene oxides form azetropes with water at atmospheric pressure. These azetropes are not readily separable by fractional distillation. Therefore, purification methods used in ethylene oxide and propylene oxide processes are not necessarily applicable to the purification of butylene oxide.

U.S. Pat. No. 2,779,721 suggests drying wet butylene oxides by liquid extraction of butylene oxide with a strong aqueous solution of an alkali metal hydroxide at a temperature below about 50° C. Up to 87% of the water can be removed from the mixture of butylene oxides containing 80% 1,2-butylene oxide and 2.3% water by this method. On the one hand, drying butylene oxide containing as little as 3.5% water by fractionation is impracticable since at least half of the oxide distills as the azeotrope before the water is removed. On the other hand, removal of water by fractionation is said to be practicable when the butylene oxide contains less than about 0.5 weight % water. Under these latter conditions, water is removed as an azeotrope containing 7% water and 93% oxide, leaving the remaining oxide dry. Because the isobutylene oxide/water azeotrope distills at lower temperatures than the water azeotropes of straight chain butylene oxides, the '721 patent further suggests that isobutylene oxide may be advantageously separated from straight chain butylene oxides by azeotropic distillation of the raffinate from the alkaline metal hydroxide extraction step. The patent teaches that the azeotropic column should be a still column having a large number of theoretical plates and that the separation be carried out under a high reflux ratio.

U.S. Pat. No. 3,338,800 teaches extractive distillation of olefin oxides having from 3 to 18 carbon atoms with a paraffin or paraffin naphtha solvent. More particularly, this patent suggests that oxygenated impurities boiling within 5° C. of the olefin oxide may be separated by extractive distillation using as solvents acyclic paraffinic hydrocarbons having boiling points at least 35° C. above the boiling points of the said purities. The problem addressed by this patent is that epoxide fractions produced by the direct oxidation of ethylenically unsaturated compounds with molecular oxygen in the liquid phase contain oxygenated impurities which, because their boiling points are similar to the desired epoxide product, cannot be separated by conventional distillation techniques. The impurities generally include acids, alcohols, aldehydes, ketones and esters. Example 3 of the patent shows extractive distillation of a crude mixture containing 85 weight % isobutylene oxide, 5 weight % ethyl formate and 10 weight % prionaldehyde with an n-octane solvent. The molar ratio of isobutylene oxide:n-octane was 1:11.5 in this example. The overhead temperature was 62° C. and the reboiler temperature was 108° C. Reflux ratio was 40:1. Also see U.S. Pat. No. 3,337,425 which teaches a process similar to the '800 patent except that olefinic naphtha and aromatic hydrocarbons having boiling points at least 35° C. above the impurities are employed as the extractive distillation agent.

U.S. Pat. No. 3,578,568 suggests purifying $C_3$–$C_5$ monoepoxides by extractive distillation with ethylene glycol, propylene glycol, ethylene glycol monomethylether or diethylene glycol monomethylethers.

U.S. Pat. No. 3,838,020 teaches a process for purifying $C_3$–$C_5$ alkylene oxides by extractive distillation using a mixed extractive solvent consisting of at least one solvent selected from the group consisting of 1,3-butylene glycol; 1,4-butylene glycol; isobutylene glycol and glycerine and at least one solvent selected from the group consisting dioxane, butylacetate and 2-ethylhexanol. The method is said to be suitable for purifying crude alkylene oxide streams containing up to about 5 weight % impurities.

An object of the present invention is an improved method for drying butylene oxides, especially straight-chain butylene oxides and particularly 1,2-butylene oxide. A further object of this invention is an improved method for purifying 1,2-butylene oxide produced by epoxidation of 1-butene with an organic hydroperoxide in the presence of the catalyst. Other objects will be apparent from the following description of the invention.

SUMMARY OF THE INVENTION

Water is readily separable from butylene oxides according to the method of the present invention by extractive distillation using selected hydrocarbon solvents. The extractive distillation solvents of this invention are acyclic, paraffinic hydrocarbons having from 7 to 9 carbon atoms and mixtures thereof. The solvents may be straight- or branched-chain, although straight chain paraffins, especially n-octane, are preferred. The solvents have been found to increase the volatility of water relative to butylene oxide. Because of this enhanced volatility, it is possible to recover essentially all of the butylene oxide fed to the column in the bottom stream. The bottom stream is essentially water-free. More than 99% of the butylene oxide present in the feed is recovered in the bottoms and more than 99% of the water and lighter impurities such as methanol and acetone are removed overhead.

In a particular embodiment of this invention, high purity 1,2-butylene oxide is recovered from a crude, water-containing fraction obtained in processes wherein 1-butene is reacted with an organic hydroperoxide in the presence of a suitable catalyst.

DETAILED DESCRIPTION OF THE INVENTION

The "butylene oxides" treated in accordance with the method of this invention are those in which the oxygen atom is bonded to each of two contiguous carbon atoms. Thus, the term includes 1,2-butylene oxide, cis- and trans-butylene oxide and isobutylene oxide. Tetrahydrofuran is not a "butylene oxide" within the meaning of the present invention. In a preferred embodiment, the method of this invention is used to purify crude 1,2-butylene oxide streams.

The present invention is broadly applicable to the resolution of mixtures containing butylene oxides and water. The amount of water present is not critical but generally the crude mixture will contain from about 2 to 5 weight % water and from about 92 to 96 weight % butylene oxide. Other impurities may also be present and will typically comprise higher- and lower-boiling oxygenated impurities.

The invention is applied with particular advantage to the recovery of high purity 1,2-butylene oxide from crude mixtures thereof obtained from processes wherein 1-butene is reacted with an organic hydroperoxide in the presence of a suitable catalyst. Such processes are known, having been described in various patents including U.S. Pat. Nos. 3,468,099 and 3,375,462. Olefins are epoxidized to form the corresponding oxirane derivative and the organic hydroperoxide is converted to the corresponding alcohol. The effluent from the reactor is processed by distillation or other methods to recover the olefin oxide and the by-product alcohol. Examples of these separation methods are described in U.S. Pat. Nos. 3,427,299 and 3,523,956.

The crude 1,2-butylene oxide mixture charged to the preferred embodiment of this invention comprises the mixture obtained by subjecting the total reaction product from the 1-butene oxidation reaction to such known treatments to effect removal of catalyst entrained from the epoxidation zone, unreacted 1-butene and the alcohol corresponding to the organic hydroperoxide. The organic hydroperoxide preferably employed in the epoxidation step is tertiary butyl hydroperoxide.

The principal impurities present in crude butylene oxide streams obtained in such processes are water, acetone, methanol, methyl acetate, ethyl acetate, methyl ethyl ketone, trans-2,3-butylene oxide and isobutylene oxide. Application of the present invention to such a stream results in substantially complete removal of water, acetone and methanol in the extraction column overhead and substantially complete recovery of butylene oxide in the extractive column bottoms. A major portion of the methyl acetate is recovered in the extractive column overhead, with the remaining methyl acetate being removed from the butylene oxide-rich bottoms in subsequent fractionations. Higher boiling impurities such as ethyl acetate and methyl ethyl ketone that may be present in the crude mixture are also removed from the butylene oxide-rich bottoms by subsequent fractionation.

The extractive distillation may be performed batchwise or continuously. The process is preferably performed continuously.

The purification can be effected in conventional extractive distillation means. The solvent is fed into a distillation tower through an inlet near the top of the tower and the crude butylene oxide is feed through an inlet near the middle of the tower. The solvent fed at the top raises the relative volatilities of water and lower boiling oxygenated impurities. The effect is to distill out impurities such as water, methanol, and acetone from the top of the tower and to discharge the product and solvent from the bottom. The mixture of solvent and product recovered in the bottoms is further separated in a series of fractionation means to recover solvent which is recycled through the extractive distillation step and high purity butylene oxide.

The molar ratio of extractive distillation solvent to butylene oxide in the crude mixture may vary broadly from about 2 to 15:1. Preferably, the ratio is within the range from about 3 to 10:1 and more preferably from about 5 to 7:1. The relative amount of solvent added to the extractive distillation zone has a significant effect on impurity removal. At lower solvent:butylene oxide molar ratios (e.g., less than 3:1), removal of impurities such as acetone and methanol is significantly reduced. At very low ratios (e.g, less than 2:1), there is a risk of forming water/butylene oxide azeotropes. Increased ester removal is obtained by operating at higher solvent:butylene oxide ratios, but since these esters are separable in subsequent fractionation steps, little improvement in overall purification efficiency is obtained at molar ratios exceeding about 7:1.

Temperatures and pressures in the extractive distillation column may be varied over wide ranges. Reboiler temperatures will generally be such that substantially all (greater than 99%) of the butylene oxide is withdrawn in the bottoms stream. Preferably, the column is operated at about atmospheric pressure, although subatmospheric and superatmospheric pressures may also be employed. As the overhead temperature approaches and exceeds 200° F., excessive loss of butylene oxide in overhead occurs, reducing butylene oxide recovery (expressed as percent of butylene oxide feed recovered in the extractive column bottoms). Accordingly, it is preferred to maintain overhead temperatures within the range from about 160° to 195° C., preferably from about 170° to 180° F. The invention is more particularly described by the following Examples. This description is illustrative and is not intended to limit the scope of the present invention.

EXAMPLE 1

Referring to the FIGURE, a crude 1,2-butylene oxide stream 1 having the composition indicated in Table I is introduced at a temperature of 150° F. and a pressure of 30 psia into extractive distillation column 10. The column 10 has 25 theoretical plates and stream 1 is introduced at the 15th theoretical plate. A stream 3 of n-octane at 150° F. and 30 psia is introduced at the top of column 10. The molar ratio of n-octane:butylene oxide is maintained at about 6:1. An overhead stream 7 having the composition indicated in Table I is withdrawn from the top of column 10 at a temperature of 175° C. and a pressure of 20 psia. A bottoms stream 8 having the composition indicated in Table I is withdrawn from the bottom of column 10 at a temperature of 237° F. and a pressure of 24 psia.

TABLE I

Typical Operation of Extractive Distillation Zone

| Compound | Stream (moles/hour) | | |
|---|---|---|---|
| | Crude Feed 1 | Overhead 7 | Bottoms 8 |
| Butylene oxides | 103 | 0.55 | 102.4 |
| n-Octane | 0 | 3.54 | 596.46 |
| Water | 13.97 | 13.97 | — |
| Methanol | 1.17 | 1.17 | — |
| Acetone | 2.18 | 2.15 | 0.02 |
| Methyl acetate | 0.78 | 0.61 | 0.17 |
| Ethyl acetate | 0.32 | — | 0.32 |
| Methyl ethyl acetone | 0.20 | — | 0.20 |
| Glycol and heavies | — | — | 0.3 |
| Total | 121.62 | 22 | 699.62 |

Note the complete removal of water and methanol from the butylene oxide-rich bottom stream 8. Moreover, note that almost 99% of the acetone is also recovered in the overhead stream. About 80% of the methyl acetate is recovered in overhead stream 7.

The bottom stream 8, containing butylene oxides, solvent and heavies passes to butylene oxide/solvent column 30 through line 9.

The overhead vapor 7 from column 10 is condensed (not shown) and the condensate is introduced into decanter 15. In decanter 15, the condensate separates to form two liquid phases: an aqueous phase and a solvent phase. The aqueous phase is withdrawn from decanter 15 through line 17 as waste. The solvent phase is withdrawn through line 19 and passes to solvent recovery column 20. If desired, a portion of the solvent phase may be returned directly to column 10 through line 18.

In another embodiment not shown in the FIGURE, water may be added to condensate 7 in a mixing zone prior to decanter 15 in order to enhance the separation and recovery of water-soluble impurities.

In addition to separating about 80% of the water-soluble impurities present in overhead stream 7, decanter 15 affords the opportunity to recover any butylene oxides which may be carried overhead from column 10 in the solvent phase 19.

Solvent phase 19 is fractionated in solvent recovery column 20 to separate an overhead stream 23 comprising methanol and acetone and a bottoms stream 26 which contains essentially all of the solvent in stream 19 and which is essentially free of impurities. The overhead stream 23 is purged from the process and the bottoms solvent stream 26 is introduced with extractive distillation column bottoms 8 through line 9 to butylene oxide/solvent column 30.

The purpose of column 30 is to separate (by fractionation) a bottom stream 33 comprising solvent and an overhead stream 37 comprising butylene oxide isomers. Typical compositions of these fractions is indicated in Table II. More than 98.5% of the 1,2-butylene oxide in feed stream 9 is recovered overhead.

The bottoms solvent stream 33 is cooled and recycled to the top of extractive distillation column 10. Make-up solvent (i.e., n-octane) may be added to line 34 as required. Small portions of solvent stream 33 are intermittently purged from the process through line 34 to control build-up of glycol and heavies in the system. A suitable method for minimizing salt losses as a result of this purge is to add the purged stream 34 to decanter 15 wherein glycol and heavies are removed in the aqueous phase 17.

The overhead stream 37 from column 30 is introduced to epoxidate column 40 wherein 1,2-butylene oxide is separated from its isomers. The isomers and remaining methyl acetate are removed in overhead stream 42 and 1,2-butylene oxide is recovered in bottoms stream 48. The efficiency of impurity removal in column 40 is greater than 96% and the recovery rate of 1,2-butylene oxide from the feed 37 is about 99%.

The small amount of heavy impurities (e.g., ethyl acetate and methyl ethyl ketone) remaining in the bottoms 48 from epoxidate column 40 are removed through line 53 in heavies column 50. The distillate 55 is 99.8% pure 1,2-butylene oxide product.

Comparative Example 2

Terminal vapor-liquid equilibrium data were obtained in an Othmer still at about atmospheric pressure for the binary system, acetone/1,2-butylene oxide. The still temperatures, liquid compositions and volatilities of acetone relative to 1,2-butylene oxide are shown in Table III.

TABLE III

| Temperature (°C.) | Liquid Composition (mole fraction acetone) | Relative Volatility |
|---|---|---|
| 56.2 | 0.9917 | 1.1 |
| 60.9 | 0.1703 | 1.4 |

Several solvent systems were tested to measure enhancement of the resulting acetone volatility relative to 1,2-butylene oxide. The systems tested were:

(a) 2-ethyl-1-hexanol/propylene glycol;
(b) 2-ethyl-1-hexanol/ethylene glycol;
(c) butyl acetate/propylene glycol;
(d) n-octane.

Only n-octane was found to increase the volatility of acetone relative to 1,2-butylene oxide.

EXAMPLE 3

Vapor-liquid equilibrium data were obtained in an Othmer still at about atmospheric pressure for the ternary system-acetone; 1,2-butylene oxide; and n-octane. Volatilities of acetone relative to 1,2-butylene oxide are shown in Table IV.

TABLE IV

| | Octane/1,2 BO (wt/wt) | |
|---|---|---|
| | 7:1 | 26:1 |
| Temperature °C. | 97.8 | 80.2 |
| Mole fraction acetone in liquid | 0.01 | 0.03 |
| Relative Volatility (Acetone/1,2-BO) | 3.1 | 2.4 |

What is claimed is:

1. A process for removing water from crude butylene oxides which process comprises extractively distilling a water-containing, crude butylene oxide stream with an added extractive distillation solvent consisting essentially of acyclic, paraffinic hydrocarbons having from 7 to 9 carbon atoms to remove water as distillate and in recovering a bottoms liquid stream comprising butylene oxide and solvent.

2. The method claim 1 wherein said extractive solvent consists essentially of a straight chain hydrocarbon.

3. The process of claim 2 wherein said distillation solvent consists essentially of n-octane.

4. The processes of claim 1 or claim 2 wherein the solvent:butylene oxide molar ratio is within the range from about 2 to 15:1.

5. The processes of claim 4 wherein the said molar ratio is within the range from about 5 to 7:1.

6. A process for purifying crude, 1,2-butylene oxide formed by liquid-phase epoxidation of 1-butene with an organic hydroperoxide in the presence of a suitable catalyst and removal of catalyst entrained from the epoxidation zone, unreacted 1-butene and the alcohol corresponding to the organic hydroperoxide, said crude 1,2-butylene oxide containing impurities comprising water, acetone, methanol, ethyl acetate, methyl ethyl ketone and isomers of 1,2-butylene oxide, which process comprises:
   (a) extractively distilling the crude 1,2-butylene oxide with an extractive distillation solvent essentially of acyclic paraffinic hydrocarbons having from 7 to 9 carbon atoms to remove impurities comprising water, methanol and acetone as a first distillate stream and recovering a first bottoms stream comprising 1,2-butylene oxide and solvent;
   (b) fractionally distilling the first bottoms stream to recover a second bottoms stream comprising solvent and a distillate stream comprising 1,2-butylene oxide;
   (c) recycling the second bottoms stream comprising solvent to step (a);
   (d) fractionally distilling the distillate stream from step (b) to recover a bottoms stream comprising 1,2-butylene oxide and a distillate stream comprising isomers of 1,2-butylene oxide;
   (e) fractionally distilling the bottoms stream of step (d) to recover a bottoms stream comprising methyl ethyl ketone and ethyl acetate and a distillate 1,2-butylene oxide product.

7. The method of claim 6 comprising the further steps:
   (a) condensing the first distillate stream comprising water, methanol and acetone;
   (b) decanting the condensed distillate to recover an aqueous phase and an solvent phase;
   (c) purging the recovered aqueous phase;
   (d) fractionally distilling the recovered solvent phase to remove impurities comprising methanol and acetone as distillate from a bottoms stream comprising solvent; and
   (e) combining the bottoms stream comprising solvent with the first bottoms stream.

8. The process of claim 6 wherein the molar ratio of extractive distillation solvent to 1,2-butylene oxide in the crude stream is within the range from about 2–15:1.

9. The process of claim 8 wherein the said molar ratio is within the range from about 3–10:1.

10. The process of claim 9 wherein the said molar ratio is within the range from about 5–7:1.

11. The methods of claim 6 or 10 wherein said extractive distillation solvent consists essentially of a straight chain hydrocarbon having from 7 to 9 carbon atoms.

12. The method of claim 6 wherein the crude 1,2-butylene oxide is formed by liquid phase epoxidation of 1-butene with tertiary butyl hydroperoxide in the presence of a suitable catalyst.

* * * * *